US007582600B2

(12) United States Patent
Markert et al.

(10) Patent No.: US 7,582,600 B2
(45) Date of Patent: Sep. 1, 2009

(54) USE OF UNSATURATED KETONES AS A PERFUME

(75) Inventors: Thomas Markert, Monheim (DE); Volker Porrmann, Hilden (DE); Frank Rittler, Duesseldorf (DE)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/263,603

(22) Filed: Nov. 3, 2008

(65) Prior Publication Data

US 2009/0054299 A1 Feb. 26, 2009

Related U.S. Application Data

(63) Continuation of application No. 10/507,203, filed on Jan. 24, 2005, now abandoned.

(51) Int. Cl.
*A61K 8/00* (2006.01)

(52) U.S. Cl. ......................................... 512/22; 568/303

(58) Field of Classification Search ................... 512/22; 568/303

See application file for complete search history.

(56) References Cited

U.S. PATENT DOCUMENTS 4,392,993 A 7/1983 Thomas et al.
4,507,225 A 3/1985 Sprecker et al.
4,548,743 A 10/1985 Sprecker et al.

FOREIGN PATENT DOCUMENTS

CH 586 551 4/1977
JP 59-205311 11/1984
JP 60-224650 11/1985
JP 5-70449 3/1993

OTHER PUBLICATIONS

Tsutomu Fujita, et al., "Synthesis of New Cyclic Ketones from Various Conjugated Diene Hydrocarbons (w/English Abstract)", Oil Chemistry, vol. 25, No. 7, 1977, pp. 429-432.
Masakazu Yamashita, et al., "New Synthesis of β-Bisabolene via 1-(4-Methyl-3-cyclohexenyl)-1-ethanone N, N-Dimethylhydrazone", Oil Chemistry, vol. 35, No. 12, 1986, pp. 1041-1043.
Watanabe et al, Chemical Abstracts, 1976, vol. 84, No. 25, XP002240121, abstract only.
Fujita, et al, Chemical Abstracts, 1977, vol. 87, No. 23, XP002240122, abstract only.
Ho, Chemical Abstracts, 1981, vol. 95, No. 7, XP002240123, abstract only.

*Primary Examiner*—John R Hardee
(74) *Attorney, Agent, or Firm*—Oblon, Spivak, McClelland, Maier & Neustadt, P.C.

(57) ABSTRACT

Unsaturated ketones of general formula (I) where the groups R1, R2, R3, R4 and R5 independently=H or 1-6 C alkyl groups, which can be saturated or unsaturated, straight-chained, branched or cyclic are characterised by an interesting and original odour characteristic with good emanation and are suitable for use as perfumes, for example in cosmetic preparations, technical products or alcoholic perfumery.

4 Claims, No Drawings

USE OF UNSATURATED KETONES AS A PERFUME

This is a continuation of U.S. patent application Ser. No. 10/507,203, filed Jan. 24, 2005, now abandoned.

FIELD OF THE INVENTION

The present invention relates to the use of unsaturated ketones of a specific structure as fragrances.

Many natural fragrances, relative to their demand, are available in completely insufficient quantities. For example, 5,000 kg of rose petals are needed to produce 1 kg of rose oil. The consequences include a greatly limited annual production worldwide and a high price. It is therefore apparent that the fragrance industry has a constant need for new fragrances that exhibit interesting scents. On the one hand, the range of naturally available fragrances can be supplemented thereby, on the other hand it is thus possible to make the necessary adaptations to the ever-changing fashion in taste. Furthermore, this makes it possible to meet the ever-increasing demand for scent enhancers for products of daily use, such as cosmetics and cleaning agents.

Moreover, there is generally a constant demand for synthetic fragrances that can be produced inexpensively and with a uniform high quality, and which have the original olfactory characteristics. In particular, they are intended to exhibit pleasant, sufficiently intense scent profiles that are as natural as possible and are novel in terms of their quality. Such synthetic fragrances are also intended to be capable of beneficially influencing the scent of cosmetics and goods of daily use. In other words, there is a constant demand for compounds that exhibit characteristic novel scent profiles while simultaneously ensuring considerable staying power, intensity of scent and strong diffusion.

Watanabe, Shoji; Fujita, Tsutomu; Suga, Kyoichi; Yokoyama, Toshiro describe in *J. Appl. Chem. Biotechnol.* 1975, 25, 733-736, the production of, inter alia, a compound that is designated as “1-(4-methyl-cyclohex-3-en-1-yl)-1-oxo-4-pentene”. It is directly and unequivocally evident to the person skilled in the art that this substance referenced as compound (IV) is incorrectly designated and that the structural formula is incorrectly reproduced. As is arrived at from the production specification disclosed on page 735—in agreement with the rest of the publication—the fact is that compound (III) was reacted with vinylmagnesium chloride. As is immediately apparent to the person skilled in the art, vinyl groups are necessarily “transferred” to (III), thus causing the resultant compound (IV) to be attributed with a formula in which the side chain is shorter by one $CH_2$ group. This likewise concurs with the fact that the additionally obtained compound (V), which is evidently produced as a result of the primary product’s further reaction with vinylmagnesium chloride, carries vinyl groups as well. Compound (IV) must therefore be designated 1-(4-methyl-cyclohex-3-en-1-yl)-1-oxo-3-butene.

Nothing is disclosed concerning fragrant characteristics or the suitability of the compounds as fragrances.

DESCRIPTION OF THE INVENTION

It was found that the compounds of general formula (I) superlatively meet the aforementioned requirements in every way and that they can be advantageously used as fragrances exhibiting diverse nuanced scents that in turn offer good staying power.

The subject matter of the present invention is, initially, the use of unsaturated ketones of general structure (I)

(I)

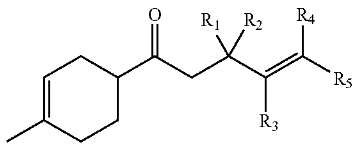

where the groups $R_1$, $R_2$, $R_3$, $R_4$ and $R_5$ independently represent H or 1 to 6 C alkyl groups, which can be saturated or unsaturated, straight-chained, branched or cyclic, for use as fragrances.

The present invention gives particular preference to the following chemical individuals of formula (I):

1-(4-methyl-cyclohex-3-en-1-yl)-4-penten-1-one (I-a)

3,3-dimethyl-1-(4-methylcyclohex-3-enyl)-pent-4-en-1-one (I-b)

1-(4-methyl-cyclohex-3-enyl)-3-propyl-pent-4-en-1-one (I-c)

In the use according to the invention, compounds (I) and, in particular, compounds (I-a), (I-b) and (I-c) can be employed individually or blended together. A particularly preferred use is that of (I-a). In another embodiment, blends of compounds (I) are used.

In a further embodiment, the invention relates to fragrance concentrates comprising one or more of the compounds of general structure (I) described above in detail.

Compounds (I) according to the invention are characterized by an odour characteristic in which fruity and herbal qualities dominate. They have excellent stability in formulations for cosmetics and perfumes of daily use.

Compounds (I) may be produced, per se, on the basis of synthesizing techniques known in organic chemistry. Particularly suitable possibilities for the production of compounds (I) can be gathered from the section dealing with the examples.

A further subject matter of the invention is a method of producing compounds of the aforementioned general formula (I).

In the presence of an acidic catalyst, 1-acetyl-4-methyl-cyclo-3-hexene or 1-(1,1-diethoxyethyl)-4-methylcyclohex-3-ene is reacted with olefinically unsaturated alkenols, the OH group of the alkenols being in alpha position relative to the C═C double bond of the alkenol. The OH group of the alcohols is preferably primary, but may also be secondary or tertiary.

In perfume compositions, compounds (I) enhance harmony and emanation as well as naturalness and staying power. Dosage is tailored to whichever scent is being striven for, while taking the composition’s other constituents into account.

It was not foreseeable that compounds (I) would exhibit the aforementioned scents, which provides further confirmation of the general experience that the olfactory characteristics of known fragrances do not permit automatic conclusions regarding the properties of structurally related compounds, since neither the mechanism of scent perception nor the effect of the chemical structure on scent perception have been adequately researched and since it therefore cannot normally be predicted as to whether a modified structure of known perfumes actually causes the olfactory characteristics to be modified or as to whether these modifications are assessed positively or negatively by the person skilled in the art.

Owing to their scent profile, formula (I) compounds are, furthermore, particularly suitable for modifying and enhancing known compositions. Particular emphasis should be placed on their outstanding intensity of scent, which contributes, in a quite general way, toward the composition's refinement.

Formula (I) compounds can be combined using numerous known fragrance ingredients, such as other perfumes of a natural, synthetic or partially synthetic origin, essential oils and plant extracts. The range of natural fragrances may include components that are both readily volatile as well as ones that exhibit medium and low volatility. The range of synthetic fragrances may include representatives of virtually any substance class.

Examples of suitable substances with which compounds (I) can be combined include in particular:

(a) Natural products such as evemia furfuraceae (tree moss) absolute, basilicum oil, citrus oils such as bergamot oil, mandarin oil, etc., mastic absolute, myrtle oil, palmarosa oil, patchouli oil, petit grain oil, absinth oil, myrrh oil, olibanum oil, cedar wood oil, sandal wood oil, East Indian, guajak wood oil, cabreuva, (b) Alcohols such as farnesol, geraniol, citronellol, linalool, nerol, phenylethyl alcohol, rhodinol, cinnamyl alcohol, Sandalore [3-methyl-5-(2.2.3-trimethylcyclopent-3-en-1-yl)pentan-2-ol], Sandela [3-isocamphyl-(5)-cyclohexanol], Mugetanol, (c) Aldehydes such as citral, Helional®, alpha-hexylcinnamaldehyde, hydroxycitronellal, Lilial® [p-tert.-butyl-$\alpha$-methyldihydrocinnamaldehyde], methylnonylacetaldehyde, (d) Ketones such as allyl ionone, $\alpha$-ionone, $\beta$-ionone, Isoraldein, methyl ionone, noot katone, Calone, $\alpha$-, $\beta$- and $\gamma$-irones, damascone, (e) Esters such as allyl phenoxyacetate, benzylsalicylate, cinnamylpropionate, citronellyll acetate, decylacetate, dimethylbenzylcarbinylacetate, ethylacetoacetate, hexenylisobutyrate, linalylacetate, methyldihydrojasmonate, vetiverylacetate, cyclohexylsalicylate, isobomylisobutyrate, evernyl, (f) Lactones such as gamma-undecalactone, 1-oxaspiro [4.4]nonan-2-one, cylopentadecanolide, ethylene brassylate, (g) Ethers such as Herbavert, ambroxan, as well as various further components often used in the perfume industry such as musk and sandal wood fragrances, indole, p-menthane-8-thiol-3-one, methyleugenol and methylanthranilate.

Noteworthy is, furthermore, how the structure (I) compounds round off the scents of a wide range of known compositions and harmonize these without, however, being dominant in an unpleasant manner.

The usable proportions of compounds (I) according to the invention, or blends thereof, in fragrance compositions range from approximately 1-70% by weight, based on the entire mixture. Blends of compounds (I) according to the invention as well as compositions of this type can be used both to perfume cosmetic preparations, such as lotions, creams, shampoos, soaps, ointments, powders, aerosols, toothpastes, mouthwash and deodorants, as well as in alcoholic perfumery (e.g. eau de cologne, eau de toilette, extracts). There is also the possibility to use the aforementioned to perfume technical products such as detergents and cleaning agents, fabric softeners and textile treating agents. To perfume these various products, the compositions are added thereto in an amount effective olfactorily, in particular in a concentration of 0.01 to 2% by weight, based on the entire product. These values do not, however, constitute limits since the experienced perfumer can still attain effects with even lesser concentrations or can construct novel complexes with even higher dosages.

EXAMPLES

Example 1

Production of 1-(4-methyl-cyclohex-3-en-1-yl)-4-penten-1-one

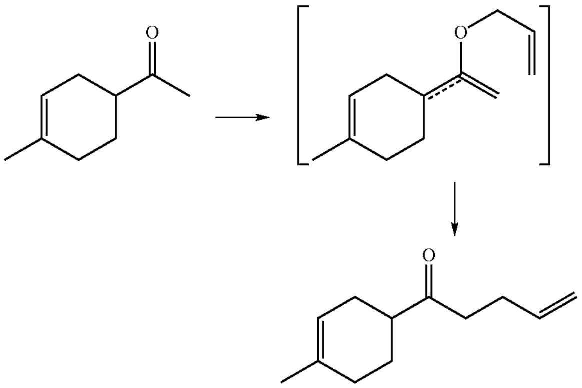

Charge:

1) 176 g (1.2 mol) 4-acetyl-1-methyl-cyclohexene (supplier: Aldrich)
2) 50 g sulphuric acid, 1% (in absolute ethanol)
3) 214 g (1.44 mol) triethylorthoformate
4) 139 g (2.4 mol) allyl alcohol Apparatus: 2-litre 3-necked flask, agitator, thermometer, nitrogen atmosphere, afterward an autoclave Execution: 4-acetyl-1-methyl-cyclohexene 1) was placed in the flask and mixed with the sulphuric acid/ethanol mixture 2) at room temperature for about 0.5 hours while being stirred and in conditions that exclude moisture. Component 3) was then added during the course of about 1 hour. The allyl alcohol (component 4) was added portion by portion. The mixture produced in this way was transferred to a steel autoclave insert and heated to 190° C. for 5 hours under 20 bar nitrogen. The GC control showed that the educt had been reduced down to 2% and that 31.5% main product had formed.

Further processing: the reaction mixture was washed neutral in a separating funnel, the organic phase was separated and dried over sodium sulphate. Low-boiling components were removed by distillation in a water jet vacuum until about 80° C. The residue of about 190 g was distilled in a 30-cm Vigreux column. The main quantity of 80 g (boiling point 50-60° C./0.2 mbar) with a GC purity of 80% was once more distilled in a Vigreux column, with 50 g of product with a purity of 95.3% being obtained.

Analysis: the IR spectrum (ATR technique) showed characteristic bands at 915, 1353, 1439, 1638, 1703 $cm^{-1}$ and a vibrational CH range of 2836 to 3074 $cm^{-1}$.

The $^1H$-NMR spectrum (400 MHz in $CDCl_3$) showed 1 methyl group (2 singlets) at 1.6 ppm and was overlapped by 1 $CH_2$ group (doublets, atom adjacent to the olefinic C atom in the cyclohexene ring on which the methyl group is located). 3 further $CH_2$ groups (2 in the cyclohexene ring and adjacent to the double bond in the side chain) showed two multiplet signals at 1.95 (intensity 4H) and 2.1 ppm (intensity 2H). The $CH_2$ group adjacent to the C═O group showed 2 very strongly split up multiplets at 2.25 and 2.35 ppm, which was overlapped by degenerate multiplets of the proton on the other side of the keto group at 2.4 ppm. The 4 olefinic protons yielded the following signals: 2 doublets (2H, terminal protons of the side chain) at 5.0 ppm, the olefinic proton in the cyclohexane ring showed a weakly split up signal at 5.35 ppm and the only olefinic proton in the side chain showed two strongly split up signals (quintets, 1H) at 5.65 ppm, overlapped.

Scent characteristic: when first smelled, Davana, fruity, green, Muguet and after 24 hours on the scent strip, the subsequent smell was faintly redolent of rhubarb.

Important: it is evident from the different scent characteristics that the compound 1-(4-methyl-cyclohex-3-en-1-yl)-4-penten-1-one produced according to example 1 of the present application differs clearly from the compound (IV) cited in J. Appl. Chem. Biotechnol. 1975, 25, 733-736 (see above) and represented therein by an incorrect structure.

Example 2

Production of 3,3-dimethyl-1-(4-methylcyclohex-3-enyl)-pent-4-en-1-one

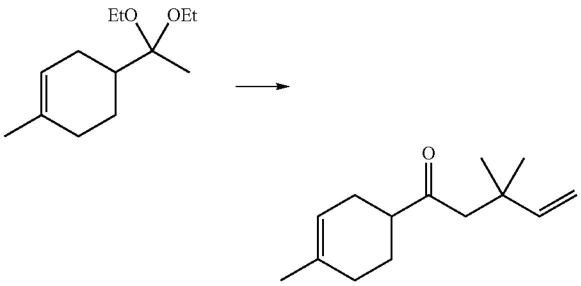

Charge:

1) 65 g (0.3 mol) 1-(1,1,-diethoxyethyl)-4-methylcyclohex-3-ene
2) 37.9 g (0.44 mol) 3-methyl-2-buten-1-ol (supplier: Aldrich)
3) 1.7 g acetic acid, concentrated
4) 1.7 g citric acid (Merck)

Apparatus: 0.5-litre agitator with thermometer, reflux cooler and water trap

Execution: components 1), 2) and 3) were placed together and stirred for 2 hours at 85° C. After addition of compound 4), they were stirred for another 2 hours at 85° C. The ingredients were cooled down to 50° C. and 2.1 g sodium methylate solution (30% in methanol) added.

The components were then carefully heated to 175° C., stirred for 3 hours and about 20 g ethanol and 3-methyl-2-buten-1-ol were removed as distillation products.

Further processing: after a GC control, it was mixed with ether, washed neutral and dried over sodium sulphate.

After being concentrated on a rotation evaporator, 56 g residue was distilled on a 30-cm packed column. 40.8 g product (boiling point 76-93° C./0.1 mbar) with a GC purity of 91.9% was isolated in the main run.

Analysis: the $^1$H-NMR spectrum (280 MHz in $CDCl_3$) showed 2 methyl groups (2 singlets, geminal methyl groups on C-3) at 1.0 ppm and 1.1 ppm. The methyl group on the cyclohexene ring showed 2 signals (each approx. 1.5Hs) at 1.55 and 1.65 ppm. The 3 $CH_2$ groups in the cyclohexene ring showed multiplet signals at 1.5 (approx. 2H) and 1.95 (intensity 4H). The $CH_2$ group adjacent to the C═O group showed 2 very differently split up signals (singlet and multiplet, 2Hs) at 2.5 ppm. The proton adjacent to the keto group and located on the cyclohexene ring appeared as a strongly split up multiplet at 2.2 ppm. The olefinc protons showed a ddd at 5.9 ppm (1H), a doublet of the doublet at 5.0 ppm (2Hs) and a broad signal for the olefinic proton in the cyclohexene ring at 5.4 ppm.

Scent characteristic: when first smelled, it was green, fruity, lardaceous, lime, and after 24 hours on the scent strip, the scent was redolent of fruit, wood, Muguet, bergamot.

Example 3

Production of 1-(4-methyl-cyclohex-3-enyl)-3-propyl-pent-4-en-1-one

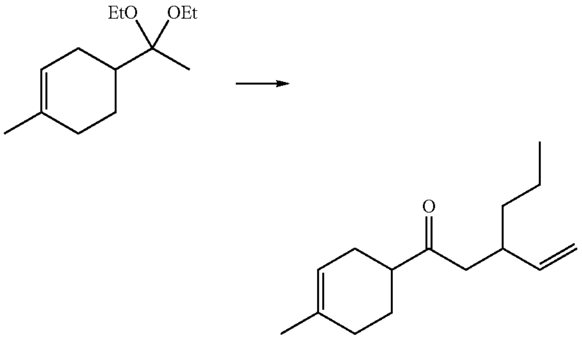

Charge:

1) 65 g (0.3 mol) 1-(1,1-diethoxyethyl)-4-methylcyclohex-3-ene
2) 44 g (0.44 mol) trans-2-hexen-1-ol (supplier: Fluka)
3) 1.1 g conc. acetic acid
4) 1.1. g citric acid (produced by the Merck firm)

Apparatus: 0.5-litre agitator with thermometer, reflux cooler and water trap

Execution: components 1), 2) and 3) were placed together and stirred for 2 hours at 85° C. After addition of component 4, the ingredients were stirred for another 2 hours at 85° C. They were cooled down to 50° C. and 2.1 g sodium methylate solution (30% in methanol) added. They were then carefully heated to 175° C., stirred for 3 hours and approx. 20 g ethanol and trans-2-hexen-1-ol were removed as distillation products.

Further processing: after a GC control, it was mixed with ether and washed neutral. It was then dried over sodium sulphate, filtered and concentrated on a rotation evaporator.

The residue of 68 g was distilled on a 30-cm packed column. 52.4 g main product (boiling point approx. 65-85° C./0.08-0.04 mbar) with a GC purity of 97.2% was obtained.

Yield: approx. 77.8 g % of the theoretical

Analysis: the $^1$H-NMR spectrum (280 MHz in $CDCl_3$) showed nearly all the signals double or three-fold. This is interpreted such that in addition to the regioisomers caused by the Diels-Alder reaction, there exist isomers that are possible as a result of the Claisen rearrangement:

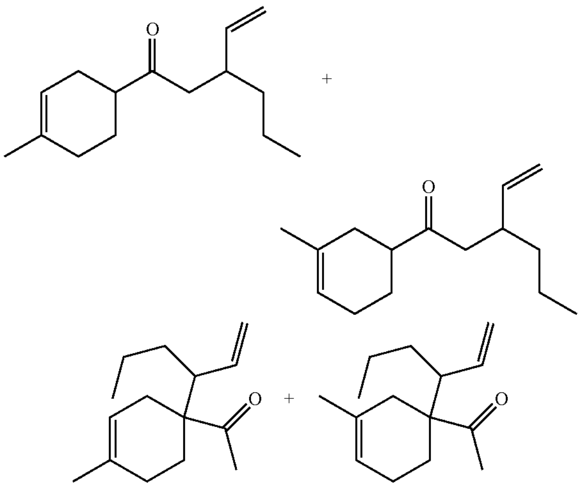

The methyl group at the end of the side chains produced a signal peak of overlapped triplets at 0.9 ppm (3Hs). Two multiplets (approx. 4Hs) were located between 1.1. and 1.4 ppm, probably they are to be assigned to the 2 $CH_2$ groups from the side chain. The methyl group on the cyclohexene ring produced broad singlets at 1.6 and 1.7 ppm (approx. 1.5Hs each). Two further signal clusters (approx. 3Hs) corresponding to a CH group and a $CH_2$ group that were adjacent to the keto group in beta position and to a double bond were found at 1.9 and 2.0 ppm. Two singlets each with one echo (approx. 4H) were at 2.1 and 2.15 ppm, and multiplets and three singlet peaks (approx. 3H) from the direct vicinity of the keto group were at 2.3 to 2.7 ppm. The olefinic $CH_2$ yielded a multiplet between 4.9 and 5.2 ppm (2Hs) and the adjacent olefinic H produced a signal group in correlation at 5.6 ppm (1H). The olefinic proton from the cyclohexene ring formed a broad singlet at 5.4 ppm (1H).

Scent characteristic: when first smelled, it was green, herbal, fresh, citrus, jasmone quality; after 24 hours on the scent strip, the subsequent smell was redolent of terpene, grapefruit, peel.

The invention claimed is:

1. A method of fragrancing a composition comprising applying at least one unsaturated ketone of formula (I)

(I)

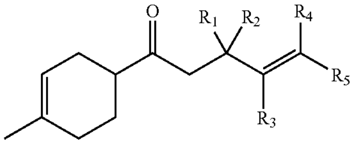

where the groups $R_1$, $R_2$, $R_3$, $R_4$ and $R_5$ independently represent H or 1-6 C alkyl groups, which can be saturated or unsaturated, straight-chained, branched or cyclic, to the composition, wherein the unsaturated ketone of formula (I) is a compound of a formula 3,3-dimethyl-1-(4-methylcyclohex-3-enyl)-pent-4-en-1-one and/or a compound of a formula 1-(4-methyl-cyclohex-3-enyl)-3-propyl-pent-4-en-1-one.

2. The method of claim 1, wherein the unsaturated ketone of formula (I) is applied in an amount from 1 to 70 wt. % based on the entire composition.

3. A compound of a formula 3,3-dimethyl-1-(4-methylcyclohex-3-enyl)-pent-4-en-1-one.

4. A compound of a formula 1-(4-methyl-cyclohex-3-enyl)-3-propyl-pent-4-en-1-one.

* * * * *

UNITED STATES PATENT AND TRADEMARK OFFICE

CERTIFICATE OF CORRECTION

PATENT NO. : 7,582,600 B2
APPLICATION NO. : 12/263603
DATED : September 1, 2009
INVENTOR(S) : Markert et al.

It is certified that error appears in the above-identified patent and that said Letters Patent is hereby corrected as shown below:

On the title page, Item (30), The Foreign Application Priority Data has been omitted. Item (30) should read:

-- (30) Foreign Application Priority Data

Mar. 19, 2002 (DE)....................................102 12 026 --

Signed and Sealed this

Tenth Day of November, 2009

David J. Kappos
*Director of the United States Patent and Trademark Office*